United States Patent [19]

Allen

[11] Patent Number: 4,867,968
[45] Date of Patent: Sep. 19, 1989

[54] ELASTOMERIC COMPOSITION CONTAINING THERAPEUTIC AGENTS AND ARTICLES MANUFACTURED THEREFROM

[75] Inventor: Dwight L. Allen, Akron, Ohio

[73] Assignee: Florida-Kansas Health Care, Inc., Olathe, Kans.

[21] Appl. No.: 138,867

[22] Filed: Dec. 29, 1987

[51] Int. Cl.$^4$ .............................................. A61K 31/74
[52] U.S. Cl. ..................... 424/78; 523/121; 523/105; 524/506; 604/96; 604/264
[58] Field of Search .................. 424/78; 524/445, 446, 524/506; 523/121, 105; 604/96, 264

[56] References Cited

U.S. PATENT DOCUMENTS

| | | | |
|---|---|---|---|
| 2,720,495 | 10/1955 | Phreaner | 260/29.1 |
| 3,695,921 | 10/1972 | Shepherd et al. | 424/422 |
| 3,962,519 | 6/1976 | Rusch et al. | 428/409 |
| 3,969,289 | 7/1976 | Coffin et al. | 260/2.5 L |
| 4,012,497 | 3/1977 | Schopflin | 424/22 |
| 4,104,322 | 8/1978 | Snavely | 260/827 |
| 4,230,686 | 10/1980 | Schopflin et al. | 424/22 |
| 4,242,287 | 12/1980 | Allen | 260/746 |
| 4,303,595 | 12/1981 | Allen | 260/746 |
| 4,303,596 | 12/1981 | Allen | 260/746 |
| 4,592,920 | 6/1986 | Murtfeldt | 427/2 |

OTHER PUBLICATIONS

C.A. 66:116533t-Netherlands Appl. 6,103,602 filed Sep. 20, 1966.
C.A. 78:75850w-U.S. National Technical Information Service, PB Rep. 1972, No. 211409.
C.A. 85:37243n-German Pat. No. 2,445,971.
C.A. 98:132388r-EPA 65,884-Urethral Catheter Capable of Preventing Urinary Tract Infection.

*Primary Examiner*—Joseph L. Schofer
*Assistant Examiner*—Carmen Pili-Curtis
*Attorney, Agent, or Firm*—Renner, Kenner, Greive, Bobak, Taylor & Weber

[57] ABSTRACT

A novel elastomeric composition of matter comprises a rubber latex and a masterbatch comprising a therapeutic agent in a therapeutically effective amount, a carrier component, titanium dioxide, and clay. A process for the preparation of a novel elastomeric composition of matter containing a therapeutic agent includes the steps of preparing a masterbatch containing a therapeutic agent, adding the masterbatch to a rubber latex and thereafter forming and curing a desired product therefrom. The composition is useful in the manufacture of rubber goods such as surgical and medical products which can be single or multilayered.

8 Claims, No Drawings

ELASTOMERIC COMPOSITION CONTAINING THERAPEUTIC AGENTS AND ARTICLES MANUFACTURED THEREFROM

TECHNICAL FIELD

This invention relates to elastomeric compositions of matter which have incorporated therein a therapeutic agent such as an antibiotic compound. The composition also comprises a migratable carrier which continually advances the agent to the surface of the elastomer. The compositions are particularly suitable for the manufacture of medical and surgical instruments such as endotracheal tubes, inhalation bags, intravenous tubing, rubber gloves, and specifically, Foley catheters, and can easily be utilized in conventional multiple-dip manufacturing processes.

Catheters, as well as other medical and surgical instruments, have customarily been manufactured from natural latex primarily because the products have a low permeability, they are easily fabricated and are relatively inexpensive. The rubber composition selected must not only be susceptible to sterilization and other cleaning operations, but it must also be able to function satisfactorily when in contact with the body and its fluids.

BACKGROUND ART

A primary concern in the health care environment is protecting the patient from infection whether endogenous, exogenous or nosocomial. One of the most common causes of hospital acquired infection arises from catheterization of the urinary tract. Even though the catheter is sterile, protecting the patient from exogenous infection, passage through the urethra to the bladder can transfer bacteria to the catheter which is then transmitted to the bladder. Other sources include the collection bag and periurethral area from which bacteria can migrate along the catheter into the bladder.

The problem is particularly prominent in long term catheterizations. Investigations have indicated that the risk of infection increase with each day of catheterization and that bacteriuria develops in almost 100 percent of chronically catheterized patients. In 1982 the Atlanta Center for Disease Control reported that approximately one-half million patients per year acquire urinary tract infections in acute care hospitals throughout the United States.

No sterile procedure known has been effective against preventing infections of this type. In an attempt to prevent infections otherwise the patient can be administered antibiotics systemically and prophylactically. While this provides some help, it is not totally effective; moreover, such methods are not without attendant problems. Another preventative step has been to apply antibacterial ointments to the shaft exterior of the catheter. However, this method provides only an initial surface treatment which is substantially removed during insertion leaving no protection for the patient with an indwelling catheter over long period of time.

One relatively recent method of controlling infections attendant the use of catheters is provided in U.S. Pat. No. 4,592,920. This patent is directed toward a method for producing antimicrobial catheters which includes the steps of suspending a comminuted antimicrobial metal compound in a curable suspending agent and then coating the catheter therewith. The suspension is then cured to bond it to the surface of the catheter.

While a bonded coating is more permanent than a topical treatment with an ointment, it would be more desirable to provide a longer acting treatment by incorporation of the desired compound directly into the latex composition, prior to curing.

The mere addition, however, is not satisfactory because the rubber latex can become destabilized preventing further manufacture or the particular additive does not remain intact during the manufacturing process or both. Of course incorporation, if successful, is of no benefit to the patient unless the desired compound can be brought to the surface of the article from within the rubber.

It is known that silicone is a material that can be compounded with rubber latex and will migrate from within the rubber to the surface. U.S. Pat. No. 3,962,519, for instance, provides for mixing silicone compounds directly into natural and synthetic rubber latex formulations prior to curing them relies upon the bleeding or migration of the silicone compound to the external surface of the instrument to provide resistance to unwanted adhesion and water repellency. The patent discloses employment of silicone compounds having a molecular weight of more than 90,000 and states that the amount present can range from about 0.1 to 10% by weight based upon the weight of the rubber. Of course, due to the migratory behavior of the silicone, the method of this patent does not permit relatively high amounts of silicone to be employed without causing separation of the silicone from the rubber latex and concomitant failure of the product.

U.S. Pat. No. 4,242,287 is directed toward an elastomeric composition comprising natural rubber latex and a silicone composition present in amounts of more than 10 to about 50 weight per 100 parts of rubber. The composition is stable and allows for continual migration of the silicone to the surface of the rubber. Articles, such as catheters, that are produced by multiple dip operations into the latex can be made without later separation of the layers.

Apart from the recognition that silicone could be incorporated into rubber compositions, there has been no incorporation of medication or other therapeutic agents into rubber compositions much less any suggestion to do so in these patents or within the existing state of the art.

Other rubber implements such as endo-tracheal tubes and rubber gloves must also be free from bacteria during use to protect exposed areas of the patient from bacteria and associated types of infection. Again, sterile procedures and topical antibacterial agents have not provided the answer.

Moreover, the threat of infectious diseases such as hepatitis, acquired immune deficiency syndrome, or AIDS, and the like have made the wearing of rubber gloves by health care workers, other than surgeons, necessary to protect the wearer. Likewise, condoms have always been proclaimed as an effective means of protecting against the spread of disease. In addition to the physical barrier provided by the rubber film, it is desirable to have incorporated into the foregoing articles various therapeutic agents that may be effective against the infectious microorganisms. While no drug has yet been found to be effective against AIDS, incorporation of such a compound into rubber gloves and condoms would be extremely helpful.

DISCLOSURE OF THE INVENTION

It is therefore an object of the present invention to provide a stable elastomeric composition containers at least a therapeutically effective amount of a therapeutic agent.

It is another object of the present invention to provide an elastomeric composition containing a therapeutic agent medicinal substance that continuously provides that agent at the surface of the elastomer.

It is yet another object of the present invention to provide surgical and medical instruments, such as Foley catheters and rubber gloves, from the elastomeric compositions disclosed herein containing a therapeutic agent.

It is still another object of the present invention to provide a process for the preparation of an elastomeric composition containing a therapeutic agent that is stable and allows the manufacture of useful surgical and medical instruments therefrom via conventional processes.

These and other objects of the present invention, together with the advantages thereof over the prior art, which shall become apparent from the specification that follows, are accomplished by the invention as hereinafter described and claimed.

In general, the preferred elastomeric composition of the present invention is prepared by preparing a masterbatch containing a therapeutic agent, adding the masterbatch to an elastomeric formulation with stirring and thereafter forming and curing a desired product therefrom. Surgical and medical products can then be formed from the therapeutic agent-containing elastomeric composition of the present invention via conventional processing techniques.

The elastomeric composition generally comprises a rubber latex formulation and from about 7.5 to 30 parts by weight of a masterbatch. The masterbatch includes, based upon the weight of the elastomer, at least a therapeutically effective amount of a therapeutic agent, at least about 3 parts by weight of a carrier component, at least about 2.5 parts by weight of clay, and at least about 1.5 parts by weight of titanium dioxide.

PREFERRED EMBODIMENT FOR CARRYING OUT THE INVENTION

Formulation of the elastomeric composition set forth herein generally includes the use of a natural rubber latex, a therapeutic agent, and a migratable carrier. Although the examples provided herein disclose the use of a natural rubber latex having 56.5% total solids content by weight, it is to be understood that other latices as well as synthetics and mixtures thereof, which have conventionally been employed in the manufacture of rubber surgical and medical instruments, can also be employed. Acceptable synthetic rubber latices include neoprene, styrene-butadiene rubber or the like. It should be noted that the aforementioned elastomeric composition may also contain conventional ingredients such as antioxidants, pigments, curing ingredients and stabilizers.

The migratable carrier is preferably employed as one component of a therapeutic masterbatch, discussed more fully hereinbelow. The carrier must have continual migrating capabilities which do not deleteriously deform the elastomeric composition. In practice of the present invention, the carrier is preferably provided by a silicone compound. Suitable silicone compounds can be selected from polysiloxanes having a viscosity of about 100 centistokes and a viscosity-average molecular weight of about 7,000, with dimethylpolysiloxane being exemplary. One particularly satisfactory silicone compound is produced by the Silicone Products Department of General Electric, and is identified by the code SM-2064. This compound is an anionic emulsion having approximately 50% total solids by weight. It requires a temperature in excess of 260 °C. to increase its molecular weight and therefore, in curing operations of the type conventionally employed in the manufacture of rubber surgical and medical instruments, it retains its low molecular weight of about 7,000.

The amount of the silicone compound added can range from at least 3 parts to about 15 parts by weight per hundred parts of rubber (phr). Greater amounts can be tolerated, as disclosed in U.S. Pat. No. 4,242,287, the subject matter of which is incorporated herein by reference; however, the higher amounts are not necessary for effective practice of the present invention.

In order to control the growth of bacteria in the area surrounding and in communication with articles made from the elastomer, the present invention provides for the addition of antibacterial agents or other therapeutic agents. A host of antibiotics are known, for instance, which have specific activity against Gram-positive bacteria such as penicillin or Gram-negative bacteria such as streptomycin, or the broad-spectrum antibiotics such as tetracycline. Other specific types include methicillin, chloramphenicol, aureomycin, terramycin, tetracyn, dimethylchlortetracycline, erythromycin, bacitracin and the like.

It will be appreciated by those skilled in the art that substantially any desired antibiotic can be employed. In fact, the present invention can provide a variety of rubber products, such as catheters, each with a different antibioltic so that the physician can select one that is effective against a particular bacteria or microorganism. Because of the unique manner in which the antibiotic is incorporated into the rubber, it remains effective despite the manufacturing and curing processes, subsequent storage, use and sterilization.

As other therapeutic agents, a wide variety of compounds may be included. Among these are cortisone and other steroids and anti-inflammatory agents; antipuretic agents; anti-fungal agents; analgesic agents; hormones and essentially any agent or drug that can be absorbed and utilized transdermally. of course, the antibiotics can be effective transdermally as well as topically i.e., surface contact effective. Spermicides may also be incorporated into condoms for a topical protection.

The foregoing agents may be added in substantially any therapeutic effective amount which provides a range of a minimal amount such as about 0.5 parts by weight per hundred parts of rubber (phr) up to any amount that does not upset the stability of the latex from which the article is to be manufactured. With specific respect to the antibiotics, the amount can be added ranges from about 0.5 to 2.5 phr. Greater amounts are not necessary inasmuch as the material constantly migrates to the surface to provide a therapeutically effective level of antibiotic. Also, amounts much higher than about 2.5 phr could upset the stability of the latex, resulting in a defective products. The antibiotic or other therapeutic agent is added via masterbatching as will be described next.

Masterbatching is a useful technique, described in detail in the aforereferenced U.S. Pat. No. 4,242,287.

The masterbatching method was first employed as a means of incorporating large amounts of silicone compounds without eventual separation from the latex or phasing in the cured elastomer. The masterbatch also contained clay and titanium dioxide. The clay is added as an aqueous dispersion having about 60% total solids by weight. Kaolin is quite suitable for this purpose and can be added in a mounts of from about 2.5 to about 8 parts by weight phr with 4.5 parts being preferred. Titanium dioxide is also added as an aqueous dispersion, having about 50% total solids content, in an amount of from about 1.5 to about 7 parts phr with 1.5 being preferred. The silicone carrier is then added in an amount of from about 3 to 15 parts with 6 being preferred.

As described in the aforementioned patent, the titanium dioxide and kaolin dispersions are combined with high speed stirring followed by the addition of the silicone emulsion at lower speeds for approximately 10 minutes. It has now been found according to the method of the present invention that dispersing the therapeutic agent in the masterbatch of the carrier and other additives is a novel and effective manner of incorporating the former into the elastomer. When added via masterbatching, the therapeutic agent is protected from any reaction with the latex as would be deleterious to the former or as would destabilize the latex. After the addition of the masterbatch to the latex and subsequent curing, the therapeutic agent is stably incorporated in the elastomeric product. The homogeneity of the masterbatch compound provides a slow and continual migration of the silicone, as such the therapeutic agent is freely carried to the surface of the elastomeric product in a continual manner an in an effective amount.

The masterbatch of the present invention is formed essentially as described hereinabove, as well as in U.S. Pat. No. 4,242,287, except for the addition of the step wherein the therapeutic agent is added to and dispersed within the other masterbatch elements. The therapeutic agent is added in the form of a dispersion to the masterbatch with slow agitation over a period of about 12 hours. Afterwards, the masterbatch is added slowly to the rubber latex at low stirring speeds, as described in the aforementioned U.S. Pat. No. 4,242,287. Depending on the amount of the therapeutic agent that is added, the total amount of masterbatch added will equal from about 7 to 30 parts phr which includes the therapeutically effective amount of agent, e.g., 0.5 to 2.5 phr in the case of antibiotics and at least 0.5 phr of other agents.

In order to demonstrate the effectiveness of the present invention, a masterbatch was prepared with and without an antibiotic, Neomyacin, as the therapeutic agent and each was added to a rubber latex formulation. The composition of the masterbatch and rubber latex compositions are presented in Tables I and II, respectively. Parts are given per 100 parts of rubber by weight.

TABLE I

| | Neomyacin Masterbatch | | | |
|---|---|---|---|---|
| | Control | Ex. 1[a] | Ex. 2[b] | Ex. 3 |
| Neomyacin | 0 | 1.5 | 1.5 | 2.5 |
| TiO$_2$ | 2.5 | 2.5 | 2.5 | 2.5 |
| Clay | 7.5 | 7.5 | 7.5 | 7.5 |
| G.E. Silicon SM-2064 | 10.0 | 10.0 | 10.0 | 10.0 |

[a]Neomyacin added to catheter balloon only
[b]Neomyacin added to entire catheter composition

TABLE II

| | Rubber Latex | | | | |
|---|---|---|---|---|---|
| Component | Parts | Percent Total Solids | C.F. | Dry Wt. (gms) | Wet Wt. (gms) |
| Rubber latex[a] | 100.0 | 56.5% | 1.027 | 1998.13 | 3632.0 |
| Zetax[b] | 0.2 | 25.0% | | 5.99 | 24.0 |
| Methyl tuads[c] | 0.3 | 35.0 | | 5.99 | 17.1 |
| ZnO | 0.4 | 50.0% | | 7.99 | 16.0 |

[a]Natural rubber latex, contains 0.7 parts sulfur
[b]Registered trademark of Goodyear Tire and Rubber Company for zinc-2-mercaptobenzothiazole
[c]Registered trademark of R. T. Vanderbilt Co., Inc. for tetramethylthiuram disulfide The masterbatch was prepared first and then added to the latex with stirring for 30 minutes. Test panels of elastomer were prepared by coagulant dipping and cured for 30 minutes at 70° C.

In order to demonstrate the effectiveness of the incorporated antibiotic, sections from the two panels were tested against the organism *Staphylococcus aureus*. To do so, a turbid suspension of the test organism was first prepared. A lawn of the test organism was applied to individual tryptic soy agar plates 15×100 mm, using sterile swabs and rotary plater. Test samples of the Control and Example Nos. 1 to 3 were placed in the center of the duplicate test plates and the plates were then incubated for a minimum of 48 hours, or until a lawn of test organisms appeared. Following incubation, zones of inhibition were measured and the zones reported in millimeters. Zones were measured from the edge of the sample to the edge of the bacterial lawn and have been reported in Table III.

TABLE III

| | Zones of Inhibition | |
|---|---|---|
| Test No. | Example No. | Effect of Neomyacin Incorporation Into Natural Rubber Latex |
| 1 | 1 | 5.5 |
| | 2 | 8.5 |
| | Control | 4.5 |
| 2 | 3 | 3.0 |
| | Control | 1.0 |

The effect of the Neomyacin incorporation into Examples No. 1 to 3 is demonstrated by the extended zones of inhibition compared to the Control samples. In Test No. 1, Neomyacin at 1.5 phr was added to the balloon dipping composition for Ex. No. 1 and the catheter composition for Ex. No. 2, and was found to be more effective in the latter instance. In Test No. 2, Neomyacin at 2.5 phr was added to the catheter composition for Ex. No. 3.

Thus it can be seen that by employing the process disclosed herein, it is possible to prepare a novel elastomer having a therapeutically effective amount of a therapeutic agent which remains homogeneously distributed throughout the rubber latex even after vulcanization. As will be apparent to those skilled in the art, the composition of the novel elastomer disclosed herein can be selected according to availability of ingredients and nature of the end product. The methods generally available for making known surgical and medical instruments can be practiced with the elastomeric composition disclosed herein which in turn can enable the worker to achieve the objects of the invention.

It should likewise be apparent that with the ability to incorporate therapeutic agents into natural and synthetic rubber latices, a variety of rubber articles can be manufactured that can be used to treat and/or protect the wearer or user as well as those with whom he or she makes contact.

It is therefore, believed that the penetration and use of the elastomers disclosed herein can be determined without departing from the spirit of the invention herein disclosed and described, the scope of the invention being limited solely by the scope of the attached claims.

I claim:

1. A homogeneous elastomeric composition of matter comprising:
    a rubber latex, said rubber being selected from the group consisting of natural rubber, synthetic rubber and mixtures thereof; and
    from about 7.5 to about 30 parts by weight, based upon the weight of 100 parts of said rubber, of a masterbatch comprising:
        a therapeutically effective amount of a therapeutic agent;
        at least about 3 parts by weight, per 100 parts of rubber, of a carrier component selected from the group consisting of polysiloxane emulsions;
        at least about 2.5 parts by weight, per 100 parts of rubber, of clay; and
        at least about 1.5 parts by weight, per 100 parts of rubber, of titanium dioxide.

2. A composition of matter, as set forth in claim 1, wherein said therapeutic agent is selected from the group consisting of antibiotics, anti-inflammatory agents, anti-puretic agents, anti-fungal agents, analgesic agents and spermicides.

3. A composition of matter, as set forth in claim 2, wherein said therapeutic agent is an antibiotic.

4. A composition of matter, as set forth in claim 3, wherein said therapeutically effective amount of said antibiotic is from about 0.5 to 2.5 parts by weight, per 100 parts of rubber.

5. A composition of matter, as set forth in claim 4, wherein said antibiotic is Neomyacin.

6. A composition of matter, as set forth in claim 5, wherein said rubber latex is natural rubber.

7. A homogeneous elastomeric composition of matter comprising:
    a rubber latex, said rubber being selected from the group consisting of natural rubber, synthetic rubber and mixtures thereof; and
    from about 7.5 to about 30 parts by weight, based upon the weight of 100 parts of said rubber, of a masterbatch comprising:
        a therapeutically effective amount of a therapeutic agent, selected from the group consisting of anti-inflammatory agents, anti-puretic agents, anti-fungal agents, analgesic agents and spermicides;
        at least about 3 parts by weight, per 100 parts of rubber, of a carrier component selected from the group consisting of polysiloxane emulsions;
        at least about 2.5 parts by weight, per 100 parts of rubber, of clay; and
        at least about 1.5 parts by weight, per 100 parts of rubber, of titanium dioxide.

8. A composition of matter, as set forth in claim 7, wherein said rubber latex is natural rubber.

* * * * *